United States Patent [19]
Botich et al.

[11] Patent Number: 6,096,005
[45] Date of Patent: *Aug. 1, 2000

[54] RETRACTABLE NEEDLE MEDICAL DEVICES

[75] Inventors: Michael J. Botich, Oxnard; Thor R. Halseth, Simi Valley, both of Calif.

[73] Assignee: MDC Investment Holdings, Inc., Wilmington, Del.

[ * ] Notice: This patent is subject to a terminal disclaimer.

[21] Appl. No.: 08/692,895

[22] Filed: Jun. 20, 1996

Related U.S. Application Data

[63] Continuation-in-part of application No. 08/381,203, Jan. 31, 1995, abandoned, which is a continuation of application No. 08/127,962, Sep. 27, 1993, Pat. No. 5,407,431, which is a continuation-in-part of application No. 08/017,832, Feb. 16, 1993, abandoned, which is a continuation of application No. 07/656,305, Feb. 15, 1991, Pat. No. 5,188,599, which is a continuation-in-part of application No. 07/378,275, Jul. 11, 1989, Pat. No. 4,994,034.

[51] Int. Cl.[7] .................................................. A61M 5/24
[52] U.S. Cl. ........................ 604/110; 604/164; 604/198
[58] Field of Search ................................. 604/110, 164, 604/192, 197, 198, 226, 240

[56] References Cited

U.S. PATENT DOCUMENTS

| | | |
|---|---|---|
| 3,306,290 | 2/1967 | Weltman . |
| 4,193,399 | 3/1980 | Robinson . |
| 4,747,831 | 5/1988 | Kulli . |
| 4,795,445 | 1/1989 | Jensen . |
| 4,813,426 | 3/1989 | Haber et al. . |
| 4,838,863 | 6/1989 | Allard et al. . |
| 4,838,869 | 6/1989 | Allard . |
| 4,850,961 | 7/1989 | Wanderer et al. . |
| 4,900,307 | 2/1990 | Kulli . |
| 4,904,242 | 2/1990 | Kulli . |
| 4,927,414 | 5/1990 | Kulli . |
| 4,966,593 | 10/1990 | Lennox . |
| 4,973,316 | 11/1990 | Dysarz . |
| 4,978,343 | 12/1990 | Dysarz et al. . |
| 4,994,034 | 2/1991 | Botich et al. . |
| 5,000,740 | 3/1991 | Ducharme et al. . |
| 5,049,133 | 9/1991 | Pascual . |
| 5,053,010 | 10/1991 | McGary et al. . |
| 5,084,018 | 1/1992 | Tsao . |
| 5,092,853 | 3/1992 | Couvertier, II . |
| 5,114,404 | 5/1992 | Paxton et al. . |
| 5,114,410 | 5/1992 | Batlle . |
| 5,125,414 | 6/1992 | Dysarz . |
| 5,129,884 | 7/1992 | Dysarz . |
| 5,180,369 | 1/1993 | Dysarz . |
| 5,180,370 | 1/1993 | Gillespie . |
| 5,188,599 | 2/1993 | Botich et al. . |
| 5,188,613 | 2/1993 | Shaw . |
| 5,201,710 | 4/1993 | Caselli . |

(List continued on next page.)

FOREIGN PATENT DOCUMENTS

WO9312830  7/1993  WIPO .

*Primary Examiner*—Corrine McDermott
*Attorney, Agent, or Firm*—Dann, Dorfman, Herrell & Skillman, P.C.

[57] ABSTRACT

Needle retraction mechanism for a medical device comprising a spring housing at the forward end of the device having an aperture for aligning a needle therein such that the needle extends forwardly out of the device. A spring is positioned concentrically about the needle and compressed within the spring housing. The needle is held within the spring housing against the expansive force of the spring by a needle retainer. The needle retainer forms the rear of the spring housing and comprises a plurality of axially extending resilient fingers. An actuating member, comprising a cavity for receiving the needle, is slidably positioned within a barrel of the device. The actuating member further comprises a forward facing shoulder surface formed to mate with rearward facing angled surfaces on the fingers. When the actuating member is urged in a forward direction within the barrel, the forward facing shoulder surface forcibly move the fingers out of engagement with the needle, thereby releasing the needle and propelling the needle into the cavity.

18 Claims, 8 Drawing Sheets

U.S. PATENT DOCUMENTS

| | | |
|---|---|---|
| 5,201,716 | 4/1993 | Richard . |
| 5,211,629 | 5/1993 | Pressly et al. . |
| 5,295,974 | 3/1994 | O'Laughlin . |
| 5,376,075 | 12/1994 | Haughton et al. . |
| 5,389,076 | 2/1995 | Shaw . |
| 5,395,337 | 3/1995 | Clemens . |
| 5,407,431 | 4/1995 | Botich et al. . |
| 5,407,436 | 4/1995 | Toft et al. . |
| 5,423,758 | 6/1995 | Shaw . |
| 5,487,732 | 1/1996 | Jeffrey . |
| 5,487,734 | 1/1996 | Thorne et al. . |

RETRACTABLE NEEDLE MEDICAL DEVICES

CROSS-REFERENCE TO RELATED APPLICATIONS

This application is a continuation-in-part of U.S. application Ser. No. 08/381,203 filed Jan. 31, 1995now abandoned, which is a continuation of U.S. application Ser. No. 08/127,962 filed Sep. 27, 1993, now U.S. Pat. No. 5,407,431, which is a continuation-in-part of U.S. application Ser. No. 08/017,832 filed Feb. 16, 1993, now abandoned, which is a continuation of U.S. application Ser. No. 07/656,305 filed Feb. 15, 1991, now U.S. Pat. No. 5,188,599, which is a continuation-in-part of U.S. application Ser. No. 07/378,275 filed Jul. 11, 1989, now U.S. Pat. No. 4,994,034. All of the drawings and descriptions of each of U.S. Pat. Nos. 4,999,034; 5,188,599; and 5,407,431 are incorporated by reference as if set forth herein.

FIELD OF THE INVENTION

The present invention relates to retractable needle medical devices and, more particularly, to a mechanism for retracting a contaminated needle in order to render a needle-bearing medical device safe after use.

BACKGROUND OF THE INVENTION

Various types of medical devices include a needle for insertion into the skin of a patient. Such needles are inserted into the skin to serve various diagnostic or therapeutic purposes. For example, a traditional injection syringe is provided with a needle for facilitating a passageway into the patient for injecting fluid into, or withdrawing fluid from, the patient. A traditional phlebotomy apparatus is provided with a needle for withdrawing fluid from a patient and transmitting the withdrawn fluid into an evacuated receptacle. A catheter stylet is provided with a needle for piercing the skin and supporting a catheter cannula on the stylet while the cannula is guided into a desired position within the patient. Each of the aforementioned needle-bearing medical devices can cause transmission of various pathogens, most notably the Human Immune Virus (HIV), due to an accidental needle stick of an uninfected person after the needle is withdrawn from the patient.

It would be desirable to provide a needle retraction mechanism for permanently and reliably retracting a used or contaminated needle into the needle-bearing medical device in order to render the medical device in a safe condition after use. It would further be desirable to provide such a mechanism in a configuration that does not interfere with the customary uses of needle-bearing medical devices, is resistant to undesired activation by forces normally encountered in the use of such medical devices, and can be easily operated without a significant change in the techniques employed by the medical professionals who use needle-bearing medical devices.

SUMMARY OF THE INVENTION

In accordance with one aspect of the present invention, there is provided a needle retention mechanism for mounting a needle to a medical device such that the needle can be retracted into the medical device subsequent to use thereof to reduce the risk of infection from an inadvertent prick. The needle retention mechanism comprises a spring housing positioned in the forward end of the device having a front alignment aperture for allowing the needle to extend therethrough from within the spring housing. A spring is positioned within the spring housing for exerting a rearward bias upon the needle. The rear of the spring housing comprises a needle retainer having axially extending resilient fingers for retaining the rearward end of the needle against the bias exerted by the spring. An actuating member is positioned within the device and has an engagement surface formed thereon for operatively engaging the rear of the spring housing to flex the resilient fingers outward in order to allow the spring to propel the needle into the interior of the device. The actuating member further has a needle receiving cavity formed therein for receiving the retracted needle.

In accordance with another aspect of the present invention, the needle retention mechanism can be adapted for retaining needles upon such medical devices as hypodermic syringes, catheter insertion devices, phlebotomy devices, and other hand-held needle-bearing instruments. In the hypodermic syringe, the actuating member provides a piston for withdrawing or injecting fluid into or from a patient. In the phlebotomy device, the actuating member is positioned within a barrel for supporting a rearward extending linking needle for piercing an evacuated fluid collection vial. In the catheter insertion device, the actuating member is fitted with a porous vent plug so that the actuating member cavity provides a blood flashback chamber for ensuring proper placement of a catheter within a patient.

Other aspects and advantages of the present invention are made apparent in the following detailed description.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

Figures 1, 3:
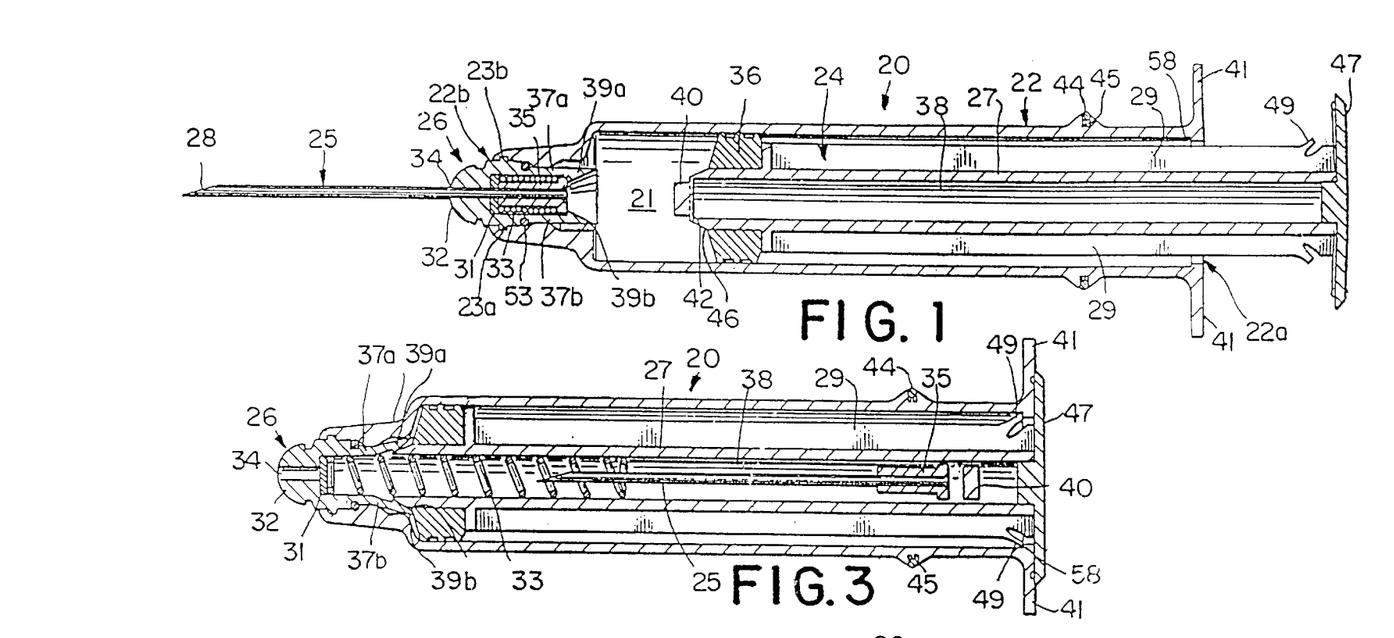
FIG. 1 is a cross-sectional view of a first embodiment of the present invention wherein the device is a hypodermic syringe and is shown with a syringe plunger in a partially depressed position within a syringe barrel.
FIG. 3 is a cross-sectional view of the first embodiment of the present invention in FIG. 1 but showing the syringe plunger in a fully depressed position and the needle fully retracted.

Referring now to FIG. 1, there is shown a syringe 20 for injecting fluid into, or withdrawing fluid from, a patient. The syringe 20 includes a hollow barrel 22. The rear end of the barrel 22 has an opening 22a formed therein for receiving an operating member, or plunger 24, in slidable engagement within interior cavity 21 of the barrel 22. The forward end of the barrel 22 is reduced in diameter and has an opening 22b formed therein for receiving a spring housing 26. A needle 25, having an axially located passageway therethrough, is axially positioned within the spring housing 26, and extends from the forward end of the spring housing 26. The forward end of the needle 25 has a pointed tip 28 for piercing the skin of a patient.

The barrel 22 has retaining lips 41 on the rear end providing a gripping surface for the user's fingers. Optionally, in a forward position from lips 41, a color coded ring 44 of sufficient resiliency and diameter is slid over the exterior surface of the barrel 22 and retained by friction to identify a particular syringe system. The color coded ring 44 is retained over the barrel 22 in circumferential groove 45. Alternatively, the ring 44 can be retained on the barrel 22 by friction. The barrel 22 is transparent, thus permitting the user to see the fluid inside so that air bubbles can be detected and expelled before the fluid is dispensed by the syringe 20.

The plunger 24 is slidably positioned as a piston within the barrel 22. The plunger 24 includes a sleeve 27 defining a central cylindrical receptacle 38 for receiving the needle 25 and needle retaining member 35 during retraction of the needle 25, and for thereafter containing the needle. Reinforcement ribs 29 extend radially outward from the sleeve 27 for maintaining the plunger 24 and the sleeve 27 in central alignment within the barrel 22 during use of the syringe 20. An annular sealing member 36 is positioned about the forward end of the sleeve 27, forming a sliding fluid seal with the interior of the barrel 22.

One or more radially extending ratchet teeth 49 interrupt the reinforcing ribs 29 and are posteriorly located while being outwardly flared to allow the ratchet teeth 49 to pass by a ratchet lip 58 on the inside of the finger retaining lip 41 of the syringe barrel 22. Upon full depression of the plunger 24 within the barrel 22, the ratchet teeth 49 pass by the ratchet lip 58. The ratchet teeth 49 flexibly pass by the ratchet lip 58 and thereafter prevent extraction or free movement of the plunger 24 from the barrel 22.

The forward end of the plunger 24 is sealed by a frangible end member 40. The frangible end member 40 is preferably integrally formed with the sleeve 27 such that a thin supporting rim 42 connects the frangible end member 40 with the forward end of the sleeve 27. The frangible end member 40 is dissociable from the end of the plunger 24 upon application thereon of a rearwardly-directed force, preferably of less than about 0.9 kg (2 pounds), sufficient to fracture the supporting rim 42.

The spring housing 26 includes a nose portion 32 having a bore 34 formed therein for holding the needle 25 in axial alignment. A washer 31 is positioned within the spring housing 26 about the rearward opening of bore 34, forming the forward interior surface of the spring housing 26 and providing a fluid seal about the shaft of the needle 25. In addition, an O-ring 53 is fitted between the spring housing 26 and the inner surface of the barrel 22 to provide a fluid-tight seal between the spring housing 26 and the barrel 22.

A needle retaining member 35 is mounted to the rearward end of the needle 25 by positioning the rearward end of the needle 25 within an axial passageway through the retaining member 35. The retaining member 35 provides an enlarged lip or outwardly extending rim relative to the diameter of the needle. The tip 28 of the needle is in fluid communication, through needle 25 and retaining member 35, with the interior cavity 21 of the barrel 22.

Within the spring housing 26, the needle 25 is surrounded by a spring 33. The spring 33 is compressed within the spring housing 26 so as to exert an expansive force between the forward interior surface of the spring housing 26 and a forward surface of the needle retaining member 35. A plurality of latching projections or fingers, of which fingers 37a and 37b are representative, extend rearwardly from the nose portion 32 of the spring housing 26 substantially parallel to the needle 25. The fingers 37a and 37b have hooks 39a and 39b formed upon the respective rear ends thereof. The hooks 39a and 39b are formed to have radially inward extending forward surfaces for engaging the needle retaining member 35 by mutual abutment between the rear surface of the retaining member 35 and the respective forward surfaces of the hooks 39. The hooks 39 are formed to have rear surfaces, or shoulders, which are angled outwardly toward the cavity 21. An annular shoulder 46 is formed at the forward end of the plunger 23. The annular shoulder 46 has a slope that is complementary to or mates with the outwardly angled surfaces of the hooks 39, in order to effect outward deformation of the fingers 37 when retraction of the needle 25 is desired. The interior of the barrel 22 is circumferentially flared in the vicinity of the hooks 39 to allow the fingers 37 to flex, or break, outwardly when the fingers 37 are deformed by the shoulder 46 of the plunger.

Attachment means, such as bayonet tabs 23 a are formed in the exterior of the spring housing 26 for engaging the spring housing 26 with mating bayonet slots 23 b formed within the forward end of the barrel 22. The bayonet tabs 23 a and slots 23 b may have complementary cambered surfaces (not shown) to allow the tabs 23 a to be permanently locked into position within the slots 23 b in a ratchet-like manner. In the use of the syringe 20, a selection of spring housings 26 having needles of various gauges may be provided for attachment to a uniformly-sized barrel 22 prior to use. After use, the selected spring housing 26 will be locked to the syringe 20 to prevent access to the retracted needle 25.

In alternative embodiments, other attachment means may be provided for the spring housing 26 and the barrel 22 such that the spring housing 26 can be attached and removed from the barrel 22. For example, it may be desirable to use different needle gauges for filling the syringe 20 from a puncturable vial and for giving the patient an injection. In such an alternative embodiment, the spring housing 26 and the barrel 22 can be provided with complementary threaded surfaces for removably attaching needles 25 of various gauges. Such threaded surfaces may be compatible with standard needle fittings, so that a standard needle housing can be used for filling the syringe. The spring housing 26 can subsequently be attached to the forward end of the barrel for giving the injection to a patient.

Figure 2:
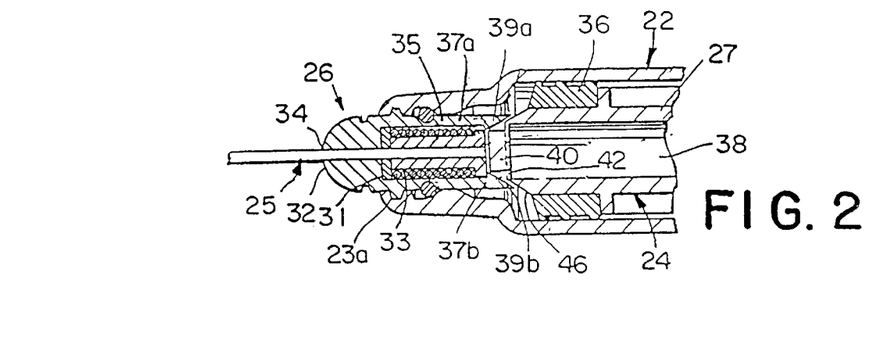
FIG. 2 is a fragmentary cross-sectional view of the front end of the first embodiment of the present invention in FIG. 1 but showing the plunger proximate to a needle housing at the forward end of the syringe.

During an injection, the user depresses a pushing plate 47 attached to the rear of the plunger 24. In this arrangement, the plunger 24 is pushed into the barrel 22 in order to expel the contents of cavity 21 through needle 25. Referring now to FIG. 2, the forward end of the syringe 20 is shown with the plunger 24 advanced within the barrel 22. At the completion of an injection stroke, the frangible end member 40 abuts against the rear surface of the needle retaining member 35. If a second injection is to be given, or if the syringe 20 is to be used to withdraw fluid from the patient, the plunger 24 may then be withdrawn within the barrel 22, while the frangible end member 40 remains intact upon the end of the plunger 24.

When retraction of the needle 25 is desired, the plunger 24 is pressed firmly into the barrel, so that the supporting rim 42 for the frangible end member 40 is fractured and the frangible end member 40 is dissociated from the end of the plunger 24. The force required to dissociate the frangible end member 40 is significantly higher than the normal force applied to the plunger 24 during an injection, so that undesired retraction is guarded against in use. When the frangible end member 40 is dissociated from the end of the plunger 24, an opening is formed through the forward end of the plunger 24 into the receptacle 38.

When the frangible end member 40 is dissociated from the end of the plunger 24, the plunger 24 may be advanced forward beyond the position shown in FIG. 2, so that the annular shoulder 46 of the plunger 24 abuts against the rearward sloping surfaces of the hooks 39. The diameter of the barrel 22 in the vicinity of the hooks 39 is sufficiently large to permit the fingers 37 to flex or break radially outward, so that the forward surfaces of the hooks 39 are moved radially outward to release the needle retaining member 35. Then, the expansive force exerted by the spring 33 propels the needle retaining member 35 and needle 25 into the receptacle 38, and indicated in the syringe 20 shown in FIG. 3.

Figure 4:
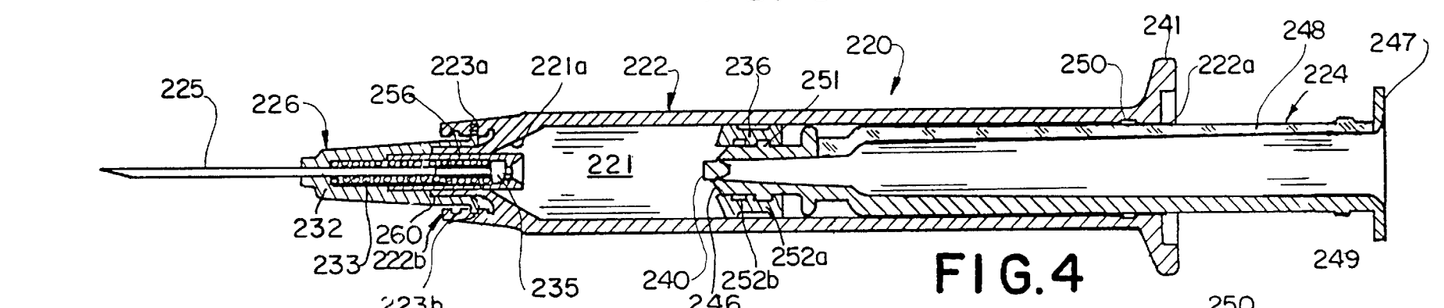
FIG. 4 is a cross-sectional view of a second embodiment of the present invention wherein the device is a hypodermic syringe and is shown with a plunger in a rearward position and ready for use.
Figure 5:
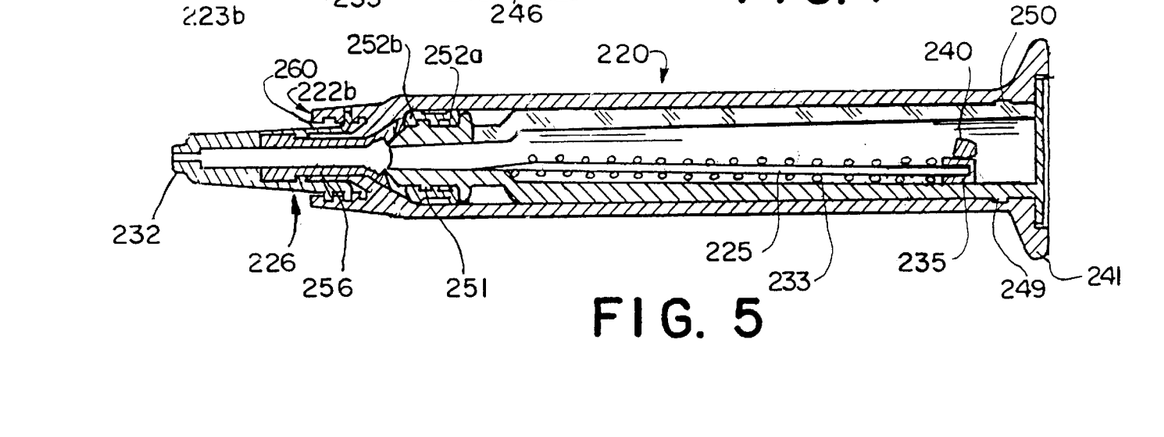
FIG. 5 is a cross-sectional view of the second embodiment of the present invention of FIG. 4 but showing the plunger in the fully depressed position and the needle fully retracted.
Figure 6:
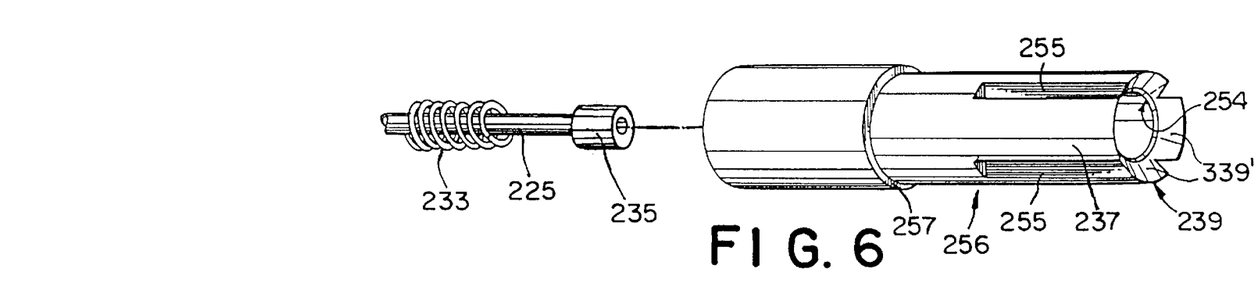
FIG. 6 is an exploded view of the rear portion of a spring housing in accordance with the present invention.

A second embodiment of the invention is illustrated in FIGS. 4–6 and consists of a syringe 220 comprising a barrel 222. The barrel 222 has a reduced diameter opening 222b at the front end and an opening 222a at the rear end. The barrel 222 has finger retaining flanges 241 near the rear end of the barrel 222 providing a gripping surface for the user's fingers.

A plunger 224 is slidably received within the barrel 222 and is sized to move linearly back and forth. The plunger 224 has a converging taper 246 on the front end and a flange 247 on the rear end. The flange 247 has a radially thinned slender section at the interface with the plunger 224 which breaks away if forced outwardly when the plunger 224 is in its fully depressed position. In addition, the shaft of the plunger 224 has a longitudinal slot or channel 248 formed therein to facilitate molding the plunger and the flange 247 as a single unit.

A frangible end member 240 is formed on the tapered end of the plunger 224. The plunger 224 further contains an outwardly extending raised circumferential band 249 around the end near the flange 247. Additionally, the barrel 222 has an internal recess 250 in a similar location near the flanges 241. When the plunger 224 is fully depressed and is recessed flush into the rear end of the barrel 222, the band 249 snaps into the recess 250 locking the plunger 224 into that location. This prevents the plunger 224 from being withdrawn and, as the flange 247 is frangible, the closure is rendered tamper-proof even if an attempt is made to pry the flange 247 from the barrel 222.

A sealing member 236 is positioned on the converging tapered end of the plunger 224. The sealing member 236 provides a resilient sliding seal for the internal cavity 221 of the barrel 222 allowing liquids to be drawn inside and forced out by reciprocating movement of the plunger 224. Initially, the sealing member 236 is positioned such that a first circumferential groove 252a formed in the interior of the sealing member 236 is held upon a radial projection 251 formed about the exterior of the tapered end of the plunger 224. When the plunger 224 is fully depressed into the barrel 222 to effect retraction of the needle, the sealing member 236 is forced over the radial projection 251 into a secondary position wherein a second circumferential groove 252b in the sealing member is received and held upon the radial projection 251, as indicated in FIG. 5. As can be appreciated, the sealing member is initially seated upon the plunger such that a forward surface of the sealing member is positioned in the forward direction beyond the rear of the converging taper 246 of the plunger 224. The exterior periphery of the forward portion of the sealing member is shaped to conform with the forward interior surface 221a of the cavity 221. Hence, when the plunger 224 is initially fully depressed into the barrel 222, but retraction has not yet been effected, the forward surface of the sealing member mates with the interior forward surface of the barrel so that substantially the entire contents of the cavity 221 is forced into the needle and ejected. Then, when retraction is effected, the sealing member is forced to move rearwardly upon the plunger in order to accommodate flexing the fingers 237 by forward motion of the plunger 224.

A spring housing 226 comprising a nose portion 232 and a needle retainer 256 is attachable to the forward end of the barrel 222. The axial cavity thus provided in the spring housing 226 is coextensive with an opening in the nose portion 232 to accommodate the needle 225 and its associated spring 233. The front portion 232 of the spring housing 226 attaches to the barrel 222 using bayonet tabs 223 a and slots 223b. The needle retainer 256 forms the rear portion of the spring housing 226 and retains the needle 225 therein by abutment with the rear of a needle retaining member 235 fixed to the rearward end of the needle.

The cooperative relationships among the needle retaining member 235, the spring 233, and the needle retainer 256 are best shown in the exploded view of FIG. 6. The needle retainer 256 includes rearward extending fingers 237 having hooks 239 formed toward the rear ends thereof. The fingers 237 are preferably flexible to permit outward movement for releasing the needle retaining member 235. It should be appreciated that the fingers 237 could be fractured when moved outwardly by the plunger to release the needle retaining member 235. The forward interior surfaces of the hooks 239 provide an engaging surface or stop 254, which extends radially inward for overlapping abutment with the rear surface of the needle retaining member 235. Accordingly, the needle retaining member 235 is held against the hooks 239 on the fingers 237 in relation to the expansive force exerted by the spring 233.

The hooks 239 are formed to have rearward facing canted or wedge-shaped surfaces 339; which extend outwardly at a rearward angle, for mating with a complementary tapered surface on the forward end of the plunger. When the fingers 237 are deformed or flexed radially outwardly, the hooks 239 move out of abutment with the rear surface of the retaining member 235. Upon this occurrence, the expansive force of spring 233 against the front surface of the retaining member 235, immediately thrusts the needle retaining member 235 and hence, the needle 225, rearwardly toward the back or rear portion of the syringe 220 and into the plunger.

The latching projections or fingers 237 within its associated hooks 239 of the needle retainer 256 are preferably joined together to form an annular latching member or rim 254 with a circular opening at the rear end. The needle retainer 256 is provided with longitudinal grooves 255 or score lines extending axially along the outside to facilitate breakage and separation of the fingers 237. The continuous rim 254 provides a seal with the rearward surface of the needle retaining member 235, so that fluid is kept out of the interior of the spring housing 226. Additionally, a radially-protruding shoulder 257 is formed around the exterior of the needle retainer 256 for abutment with a complementary ridge 260 on the interior of the nose portion 232 of the spring housing 226 (as best shown in FIGS. 4 and 5) to secure the needle retainer 256 to the nose portion 232 and to prevent the needle retainer 256 from being pushed rearward by the expansive force of the compressed spring 233.

In operation, fluid is drawn into the syringe 220 in a normal manner by the vacuum created when the plunger 224 is withdrawn within the barrel. After injecting the fluid, the needle 225 is withdrawn from the patient and the plunger 224 is forced completely into the barrel 222. As the tapered end of the plunger 224 is forcibly depressed against the forward end of the hollow barrel 222, the sealing member 236 is forced back over the raised projection 251, and the frangible end of the plunger is broken off. Simultaneously, the plunger's (224) converging tapered surface 249 forcibly breaks apart or moves radially outwardly the resilient fingers 237 of the needle retainer 256. This forcible bending outward of the resilient fingers 237 releases the retaining member 235 held by the hooks 239 at the end of the fingers 237 of the needle retainer. This releasing movement permits the expansive force of the coiled spring 233 to drive the needle 225, frangible end 240, and spring 233 into the hollow of the syringe plunger 224, thereby fully retracting the needle 225 and retaining it safely inside the syringe 220. An audible clicking sound is heard when this action takes place. The plunger 224 is then fully inserted into the barrel 222 with the flange 247 flush with the open rearward end 222a of the barrel 222 and is unremovable due to the locking into place of the rim 249 into the grove 250.

Figure 7:
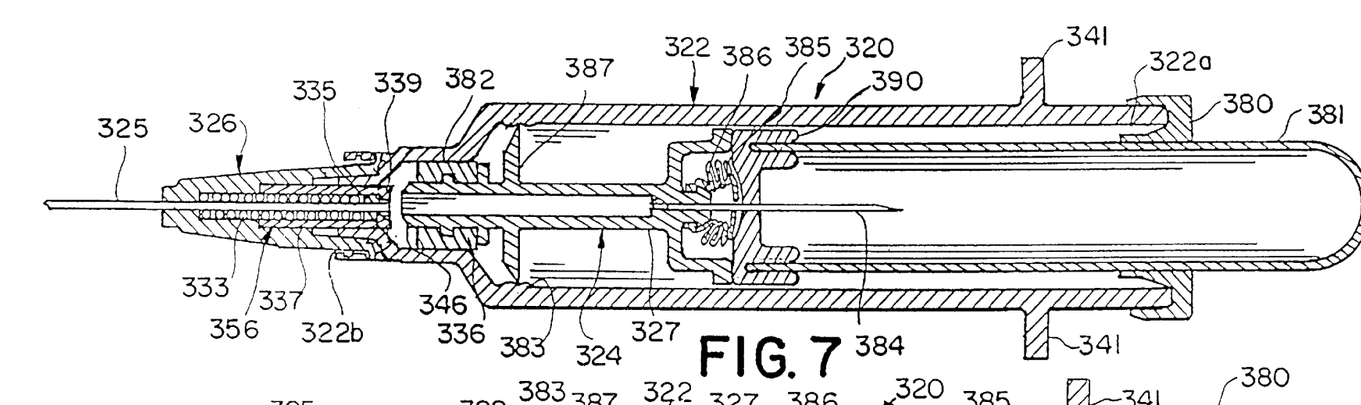
FIG. 7 is a cross-sectional view of a third embodiment of the present invention wherein the device is a vacuum tube blood sampling device and is shown with a vacuum tube installed in the device and a hypodermic needle extended and ready to use.
Figure 8:
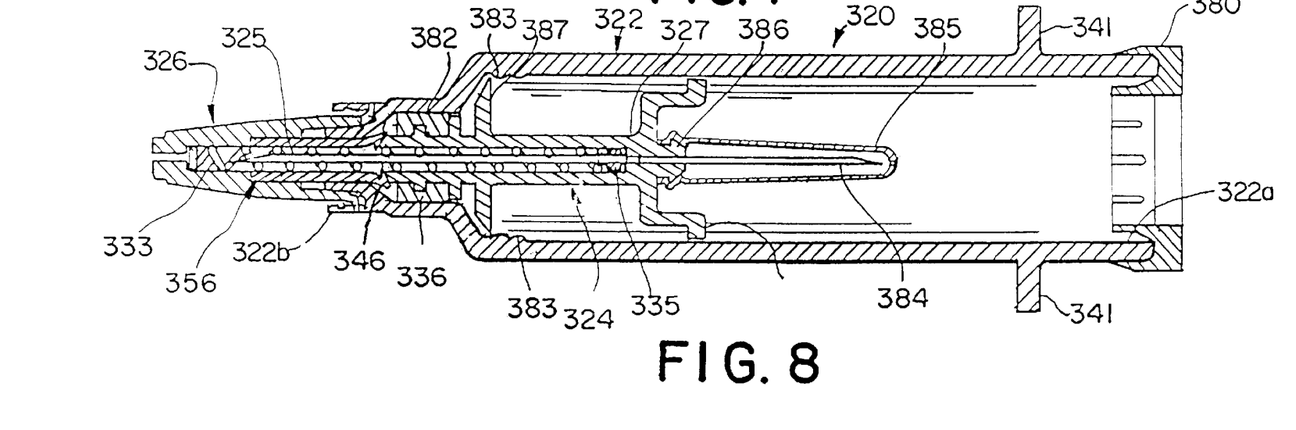
FIG. 8 is a cross-sectional view of the third embodiment of the present invention of FIG. 7 but with the vacuum tube removed and the needle retracted and ready for disposal of the device.

In a third embodiment, the invention is directed to removing fluid samples, such as blood, from the body of a patient. A phlebotomy device 320 used in taking body fluid samples in accordance with the present invention is illustrated in FIGS. 7 and 8 and comprises a hypodermic needle 325, coiled spring 333, and a spring housing 326 having resilient fingers 337 and hooks 339, in an arrangement as described in connection with the first and second embodiments.

The barrel 322 is cylindrical in shape and has a fully open end 322a and an opposed reduced-diameter end 322b. The open end 322a may optionally contain a replaceable centering washer 380 that fits over the open end 322a and that has a predetermined inside diameter allowing a single barrel 322 to be used with various diameter fluid sampling receptacles 381. Finger retaining flanges 341 are positioned away from the open end 322a to assist the user in handling and manipulating the device 320 and allowing the washer 380 to be installed on the extreme open end 322a. The reduced diameter end 322b of the barrel 322 includes a reduced tubular bore section 382.

A hollow plunger 324 is slidably received within the barrel 322. The plunger 324 is configured to provide a converging tapered surface 346 on the front end and on its rear end to hold a hollow linking needle 384. The tapered end of the plunger 324 includes a resilient sealing member 336, that snaps over the plunger 324, which slides within the reduced tubular bore section 382, to create a tight hermetic seal with sufficient resistance to maintain the seal when slid linearly in the bore section 382.

On the inside surface of the barrel 322, near the reduced-diameter end 322b, are located a pair of circumferential projections 383 that are formed about the interior of the barrel. These projections 383 are integrally formed with the barrel 322 and function as a retainer for a radial flange 387 formed on the plunger 324, the flange 387 being snap released from the projections as the plunger moves forward.

The linking needle 384 is held within the plunger 324 through a compression fit and is axially aligned within the barrel 322 as shown in FIGS. 7 and 8. A needle boot 385 is disposed over the needle 384 and stretches over a barbed projection 386 integral with the plunger 324 for holding the linking needle 384 and providing a gripping surface for the boot 385. The boot 385 is formed of a thin resilient material, such as flexible silicone, and is sized to enclose and protect the linking needle 84 when the device 320 is stored.

During operation of the device 320, a fluid sampling receptacle 381, such as a container, vial or "VACUTAINER" as it is known in the medical field, is inserted inside the open end 322a of the barrel 322. The receptacle 381 has a resilient perforatable seal 390 on one end, its inner end, and has a closed dome shaped on the other, much like a test tube. The receptacle 381 is normally fabricated of glass or transparent thermoplastic and is evacuated on the inside allowing the sampled fluid to displace the vacuum.

In operation, the hypodermic needle 325 is inserted, usually intravenously, into the patient. The receptacle 381 is then urged forward into the barrel 322 so that the linking needle 384 pierces the perforatable seal 390 and the vacuum within the receptacle 381 draws the fluid into the receptacle 381. The receptacle 381 may be removed and replaced if another sample of fluid, such as blood, is required. When finished withdrawing fluid, the device 320 is withdrawn from the patient. To effect needle retraction, the receptacle 381 is then urged further into the barrel 322 toward the partially open end 322b by the practitioner's thumb while grasping the flanges 341 with his or her fingers. This compressive force overcomes the resistance of the projections 383 holding the extended flange 387, thereby allowing the plunger 324 to slide farther forward. The tapered outer edge of rim 346 on plunger 324 forcibly spreads the resilient fingers 337 of the needle retainer 356 radially outward to release the needle retaining member 335. In this arrangement, the expansive force of the coiled spring 333 pushes the needle 325 and retaining member 335 into the hollow plunger 324. This triggered movement fully retracts the needle 325 into the hollow center of the plunger 324 and retains it in that position by the continual urging of the spring 333. An audible clicking sound is emitted when this action is completed and the receptacle 381 may then be removed. The needle 325 is thus harmlessly retained inside the device 320 and disposal of the device may be safely achieved.

Figure 9:
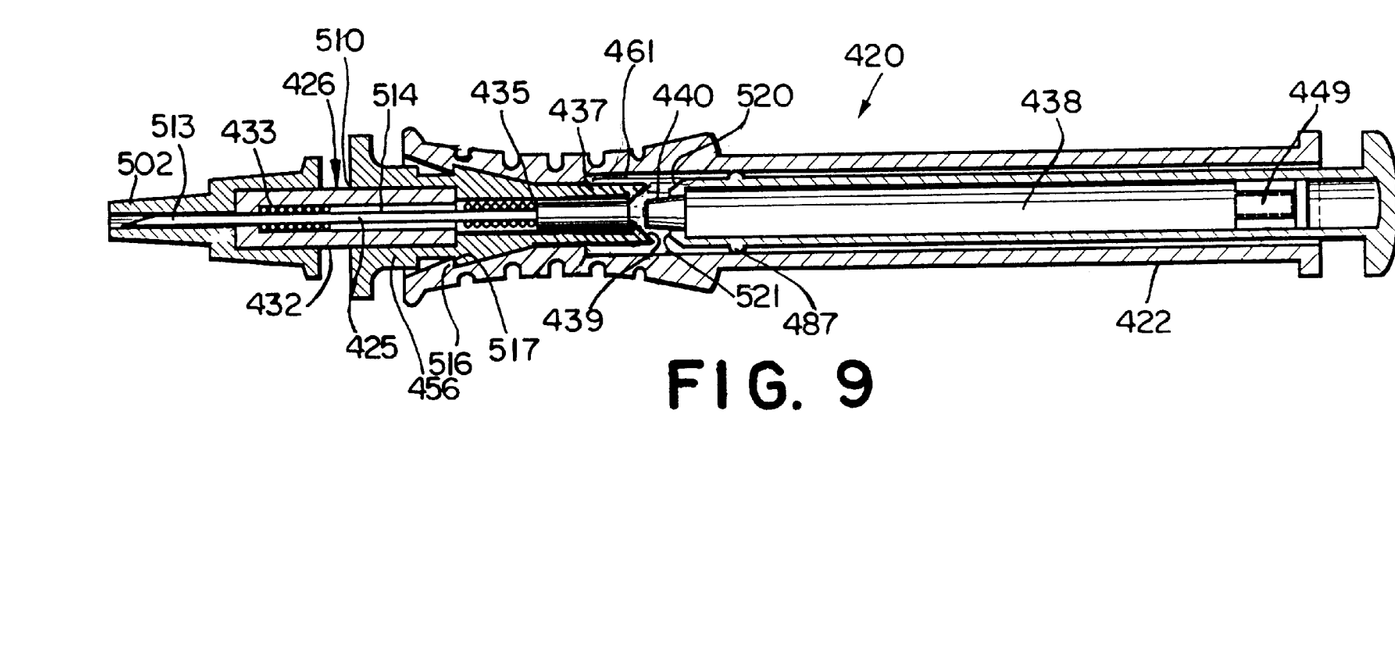
FIG. 9 is a cross-sectional view of a fourth embodiment of the present invention wherein the device is an intravenous catheter insertion device and is shown with a plunger in a partially depressed position within the barrel.
Figure 10:
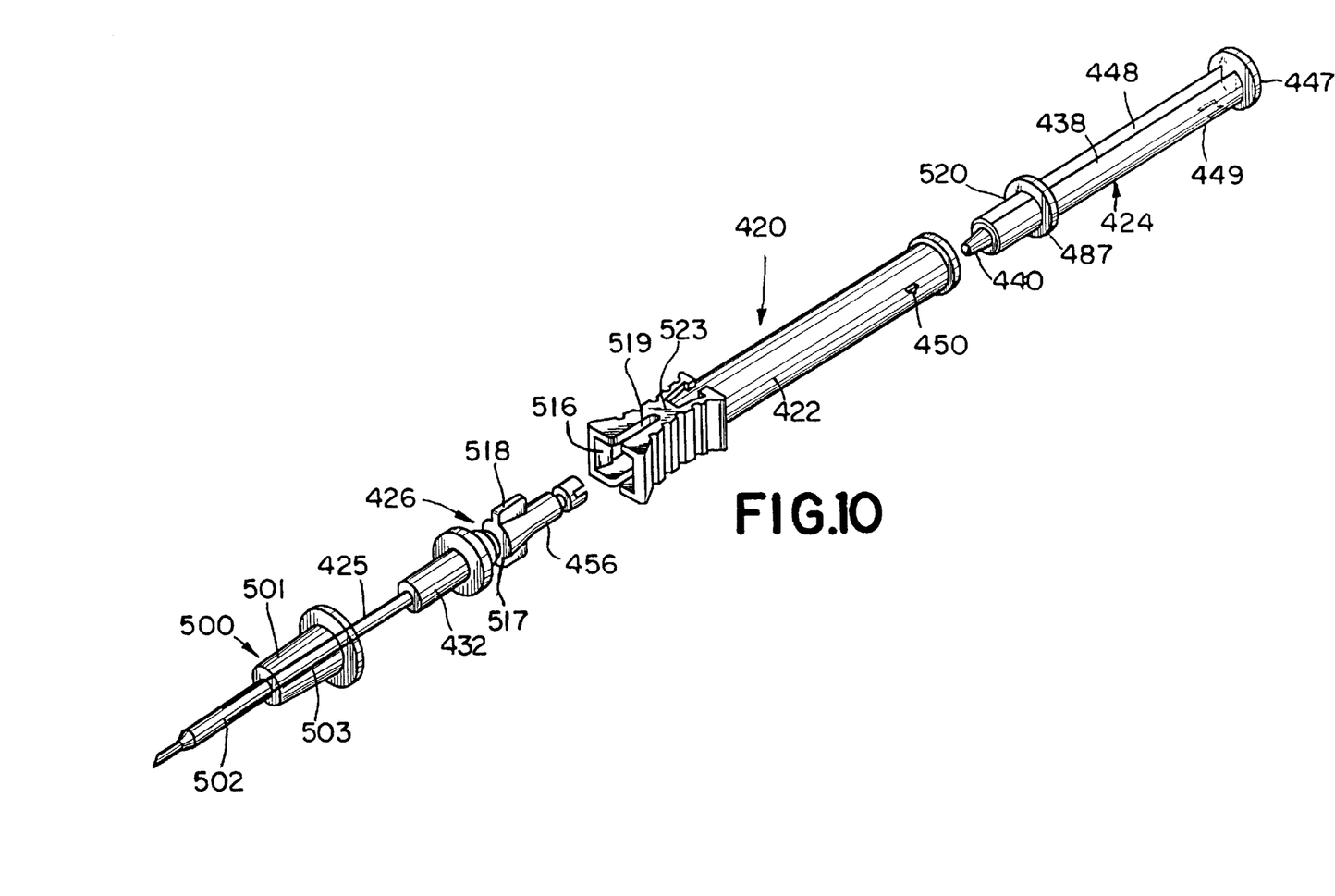
FIG. 10 is an exploded view of the fourth embodiment of the present invention of FIG. 9.

A fourth embodiment of the invention is an intravenous catheter insertion device 420 as illustrated in FIGS. 9 and 10.

Referring now to FIG. 10, the catheter 500 comprises a catheter hub 501 having an interior shaft 503 with an axial passageway. A flexible catheter sleeve 502 is attached at the front end of the catheter hub 501. The catheter 500 is positioned with the front end of a standard insertion needle 425 concentrically located within the axial passageway of the shaft 503. The rearward end of the insertion needle 425 is mounted in a spring housing 426 which engages a barrel 422. A plunger 424, having an offset extended flange 487 sized to be received within the barrel 422 for sealing purposes, is received within the rear of the barrel. For ease of manufacturing, the longitudinal cavity 438 within the plunger may have a longitudinal slot 448 formed along a side of the plunger 424. The forward end of the plunger 424 has a frangible end member 440 formed thereon.

Between the frangible end member 440 and the longitudinal cavity 438 are outwardly tapered conical shoulders 520 having a circumferential space or annular groove 521 of a defined depth which facilitate the frangible end member 440 being dissociated from the outwardly tapered conical shoulder 520. The circumferential groove 521 can, of course, simply be provided by a thinner wall of material allowing frangibility. A flange 447 is formed on the rear end of the plunger 424. The flange 447 is sized to allow the thumb or palm of the user to properly depress the plunger 424 when positioned within the barrel 422, as shown in FIG. 9.

An extending band or rachet tab 449 is rearwardly located on plunger 424, and is rearwardly flared to allow the rachet tab 449 to pass by a mating groove 450 formed in an interior wall of the barrel 422. Upon full depression of the plunger 424 within the barrel 422, the rachet tab 449 flexibly passes by the mating recess or groove 450, facilitating a locking engagement and thereby preventing the extraction of the plunger 424 from the barrel 422.

As best shown in FIG. 9, spring housing 426 comprises a front portion 432 and a rear portion provided by a needle retainer 456. A needle retaining member 435 is affixed to the rearward end of insertion needle 425 for positioning within spring housing 426. An opening 510 in the front end of the rear portion 456 of spring housing 426 is sized to receive the portion 432 of spring housing 426. Portion 432 has an aperture therein to align the insertion needle 425 and also has a cylindrical cavity 514 formed therein having a diameter to receive spring 433 coiled about the needle 425.

The needle retaining member 435 is retained by resilient fingers 437 of the spring housing 426 by radially inwardly positioned hooks 439 thereof sized to engage and hold the rear end of needle retaining member 435. The spring 433 is positioned axially within the cylindrical spring housing 426 and concentrically located around insertion needle 425. The front portion 432 compresses the spring 433 within spring housing 426 with the shaft 513 of insertion needle 425 passing through the forward aperture of the portion 432. The portion 432 is permanently affixed to the rear portion 456 of spring housing 426, as by sonic welding, bonding, or other known techniques.

As best shown in FIG. 10, the barrel 422 has internal ratchet teeth 516 sized and positioned to receive an external circumferential locking groove 517 of the spring housing 426. Barrel 422 also comprises a transparent viewing window 523 for the doctor or nurse to view fluid as it enters the barrel 422, which indicates that the insertion needle 425 and catheter sleeve 502 are located properly in a blood vessel of a patient. The spring housing 426 has external extending tabs 518 that are positionable into complementary longitudinal slots 519 of the barrel 422 for insuring proper alignment of the insertion needle 425 when the spring housing 426 is engaged with the barrel 422.

In operation, the intravenous catheter insertion device 420 functions as follows. After positioning the insertion needle 425 and catheter sleeve 502 below a patient's skin in a vessel, the insertion needle 425 is withdrawn after the health care worker sees blood in the viewing window 523. As can be appreciated, the portion of the barrel between the rear of the spring housing and the forward end of the actuating member provides a flashback chamber beneath the viewing window 523. To retract needle 425, the plunger 424 is pressed into barrel 422 causing the dissociation of the frangible end member 440 from the outwardly tapering shoulders 520 of the plunger 424. Such continued motion of the plunger causes the resilient fingers 437 to flex or break, thereby resulting in release of the needle retaining member 435. Accordingly, the compressed spring 433 exerts an expansive force against the needle retaining member 435, propelling the needle retaining member and insertion needle 425, as well as the dissociated frangible end member 440 into the longitudinal cavity 438 of the plunger 424. The above operation makes a very distinctive clicking sound, thereby assuring the health care worker that the device 420 is now safe.

As shown in FIG. 9, a circumferential chamber 461 adjacent the resilient fingers 437 by the inner diameter of the barrel 422, allowing the resilient fingers 437 to flex outwardly or break, thereby facilitating release of the needle retaining member 354. The resilient fingers 437 will only flex or break when the tapered surfaces of the hooks 439 are engaged by the tapered conical shoulders 520 of plunger 424.

In an alternative embodiment, the frangible end member 440 may be eliminated. In such an embodiment, the plunger 424 defines an aperture of sufficient size to allow the needle retaining member 435, insertion needle 425, and compressed spring 433 to be propelled into longitudinal cavity 438 when the resilient fingers 437 are flexed or break.

Returning to FIG. 10, upon further depression of the plunger 424 into the barrel 422, the rachet tab 449 engages the radial groove 450, thereby preventing the plunger 424 from being extracted from the barrel 422.

Figure 11:
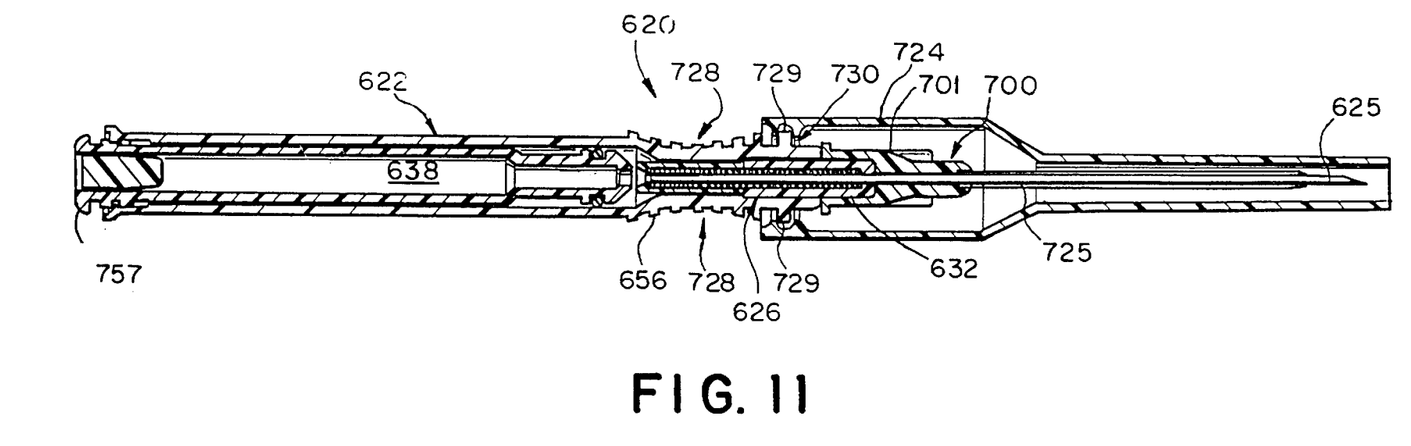
FIG. 11 is a sectional view of a fifth embodiment of the present invention wherein the device is a catheter insertion device.
Figure 12:
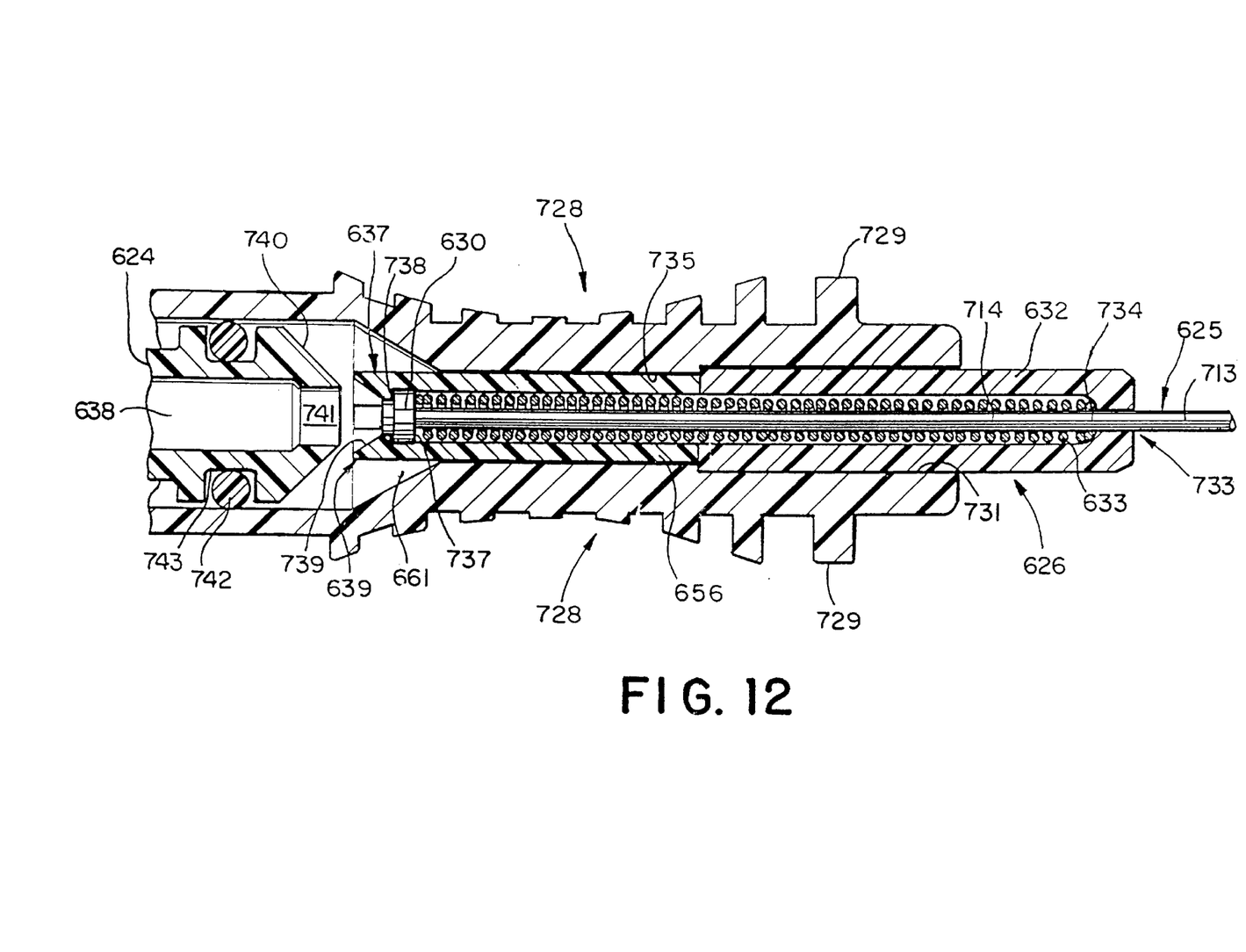
FIG. 12 is an enlarged fragmentary cross-sectional view of the front end of the fifth embodiment of the present invention of FIG. 11 but showing the protective cap and the catheter removed.
Figure 13:
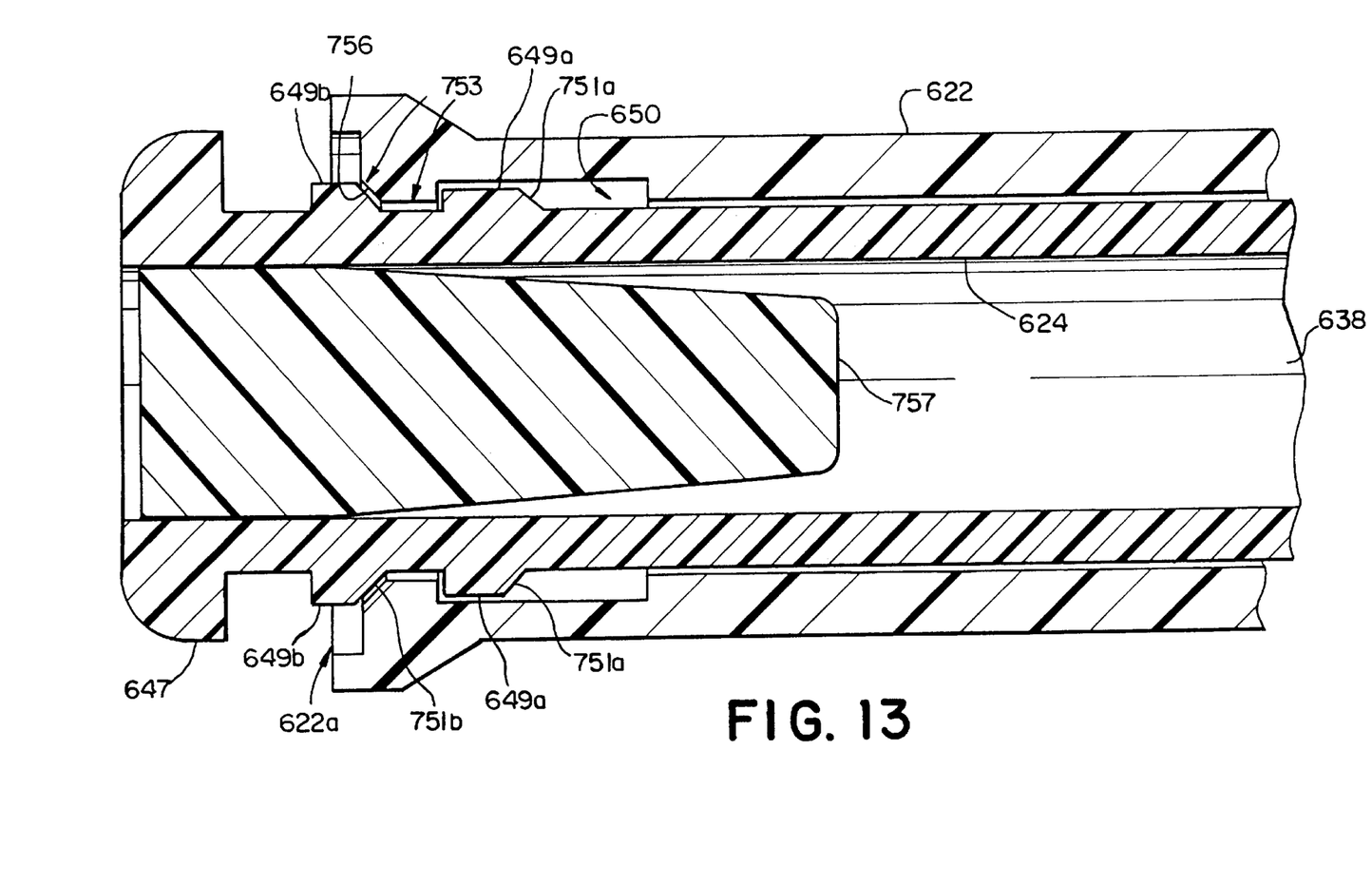
FIG. 13 is an enlarged fragmentary sectional view of the rear end of the fifth embodiment of the present invention of FIG. 11.

A fifth embodiment of the present invention is shown in FIGS. 11–13. The device 620 may be referred to as a trocar or stylet. The device 620 includes a hollow barrel 622 of varying cross section with a spring housing 626 mounted in the front end of barrel 622. The spring housing 626 comprises a nose portion or front alignment member 632 and a rear portion providing a needle retainer 656. A needle 625 extends from the front end of the spring housing 626. A catheter 700 is mounted upon the needle. The catheter 700 includes a tapered flexible cannula 725 positioned as a sleeve over the needle 625. The tip or front end of the needle 625 extends beyond the front end of the cannula 725. The catheter 700 further includes a catheter hub 701 attached to the distal or rear end of the cannula 725. The exterior of the alignment member 632 is contoured to mate with the interior of the catheter hub 701 and removably holds the catheter 700 and its associated hub 701 in frictional engagement therewith before the catheter 700 is inserted for use in the patient.

Finger ridges 728 are formed on opposite sides of the forward end of the barrel 622. The ridges 728 are contoured to allow a doctor or other health care professional to comfortably grip the device 620 near the forward end thereof, preferably between the thumb and forefinger of the doctor's preferred hand.

Cap retaining ridges 729 are formed upon the forward end of the barrel 622, in front of the finger ridges 728, for retaining the cap 724 upon the device 620. Preferably, cap 724 is retained in snap-fit engagement thereon by a retaining groove 730 formed on the interior surface of the hollow cap 724. The cap 724 extends forward from the front end of the barrel 622 to surround and protect the needle 625 prior to use of the device 620.

Referring now to FIG. 12, the front or forward end of the barrel 622 is shown in greater detail. The front end of the barrel 622 has an axial bore 731 formed therein. The axial bore 731 is sized to receive the front alignment member 632. The front alignment member 632 is firmly engaged within the forward portion of the axial bore 731 by a friction fit. The positioning of the alignment member 632 within the front portion of the axial bore 731 may be further secured by epoxy or ultrasonic welding. The alignment member 632 is generally cylindrical and has a cylindrical axial cavity 714 with a reduced diameter portion 733 providing an opening adapted to accommodate the needle 625. The reduced diameter portion 733 also provides an internal annular surface 734, which functions as an abutment for the forward end of a compressed spring 633.

The rear end of the front alignment member 632 abuts against a reduced diameter portion 735 of the axial bore 731 through the forward end of the barrel 622. The needle retainer 656 of spring housing 626 is firmly held in the reduced diameter portion 735 of barrel 622. The forward end of the rear portion 656 of spring housing 626 abuts against the rearward end of the front alignment member 632. The rear end of the spring housing 626 is provided with a latch means, such as a plurality of fingers 637 formed at the rear end of the spring housing 626. The fingers 637 extend rearwardly from the spring housing 626 into an outwardly tapered portion 661 of the interior of the barrel 622. The fingers 637 have hooks 639 integrally formed at their ends. The hooks 639 extend radially inward for retaining the needle 625 in position, as described above. In the present preferred embodiment, four fingers 637 are employed, but more or less latching projections 637 may be used depending on the size of the device 620, the nature of the spring 633.

The needle 625 includes a needle shaft 713 and an increased diameter head 630 attached thereto. The head 630 of the needle 625 functions as a cooperating latch member with the latching projections on fingers 637. The needle head 630 includes an enlarged portion having an annular forward surface 737 which provides an abutment for the rear end of spring 633. Hence, the spring 633 is maintained in compression between the forward surface of the needle head 630 and the rearward interior surface of the front alignment member 632, to bias the needle 625 toward the rear of the device 620.

The needle head 630 further includes an abutment surface 738, which is formed as a lip or rim that is maintained in abutment with the hooks 639 of fingers 637. As should be appreciated, when the fingers 637 are deformed or flexed radially outward, the engaging surfaces of the hooks 639 would be moved out of abutment with the abutment surface 738 of the needle head 630. Upon this occurrence, the compressive force of spring 633 against the forward surface of the needle head 630, would immediately thrust the needle head 630, and hence the needle 625, through an aperture 741 in the forward end of plunger 624 toward the rear of the device 620.

A plunger 624 is slidably positioned within the barrel 622 for effecting such disengagement of the fingers 637 to free the needle head 630 and, thereby, fully retract the needle 625 into the device 620. The forward end 740 of the plunger 624 is contoured or wedge shaped to mate with cooperating wedge shaped surfaces 739 of the hooks 639. Such an arrangement facilitates the spreading of the fingers 637 to release the needle head 630. More specifically, the plunger 624 preferably has a tapered forward end 740 which engages complementary sloping faces 739 of the hooks 639, when the plunger 624 is urged forward within the barrel 622. The forward motion of the plunger 624 causes the fingers 637 to spread radially outward by flexing or breaking, thus releasing the head 630 of the needle 625.

An O-ring 742 is held in an annular recess 743 around the front end of the plunger 624 to be in sliding engagement between the plunger 624 and the interior of the barrel 622. The O-ring 742 helps to maintain the aperture 741 in alignment with the needle head 630 for unhindered retraction of the needle 625. Alternatively, the plunger 624 may be formed to fit within the barrel 622 and to maintain alignment therein by an integral sliding seal.

Referring now to FIG. 13, a vent plug 757 is positioned within the opening of the rear end of plunger 624 and is adapted to seal the rear of receptacle 638. The vent plug 757 is preferably formed of a resilient porous material that allows air to escape from within the receptacle 638 during a blood return. The vent plug 757 is preferably adapted to become clogged when wet so as to prevent any leakage of blood from the rear end of the device 620. Hence, a flashback chamber is provided by the central cavity of the actuating member. In alternative embodiments, the rear end of the receptacle 638 may be sealed with a solid sealing member, as long as the receptacle 638 is of sufficiently large volume that blood return is not significantly hindered by the back pressure produced therein when the volume is reduced by the influx of blood.

Prior to, and during insertion of the device 620 into the patient, the plunger 624 is maintained at a fixed, partially depressed position within the barrel 622, so that the needle 625 is not prematurely retracted. Additionally, it is preferable for the plunger 624 to remain locked within the barrel 622, at a second or forward position after the needle 625 is retracted into the device 620, in order to prevent access to the contaminated or used needle. Both of these objectives are attained by the dual-position locking mechanism provided at the rear end of the device 620, as shown most clearly in the enlarged view in FIG. 13.

The rear of the barrel 622 has an open end 622*a* to receive the plunger 624 within the barrel 622 during assembly of the device 620. The plunger 624 has first locking tabs 649*a* thereon, which extend outward from the exterior of the plunger 624, as in the form of a rim or tooth. The first locking tabs 649*a* extend slightly beyond the internal diameter of the barrel 622 and have sloping forward surfaces 751*a* thereon, to allow the tabs 649*a* to be forced or press-fitted into an internal circumferential groove 650 formed in the interior surface of the barrel 622. A lip 753 is formed in the interior of the barrel 622 between groove 650 and the open end 622*a* of the barrel 622. Second locking tabs 649*b* are formed on the exterior of the plunger 624 around its circumference, the second locking tabs 649*b* being located to the rear of the first locking tabs 649*a*. When the plunger 624 is positioned within the barrel 622 during assembly of the device 620, the lip 753 is caught between the rear surfaces of the first locking tabs 649*a* and the forward surfaces 751*b* of second locking tabs 649*b*. Hence, the plunger 624 is held at a first fixed position within the barrel 622 for initial use of the device 620 in insertion of the catheter 700.

The forward surfaces 751b of the second locking tabs 649b are angled or ramped to mate with complementary angled rearward surfaces 756 of the lip 753. To retract the needle 625, the plunger 624 is pushed or urged forward within the barrel 622 with sufficient force to cause the second locking tabs 649b to enter the barrel 622 by virtue of a radial deforming force exerted mutually between the angled surfaces 751b of the second locking tabs 649b and the angled surfaces 756 of lip 753. Continued forward motion of the plunger 624 within the barrel 622 is eventually halted by abutment of the rear end of the barrel 622 with an enlarged annular flange 647 forming the rear end of the plunger 624. When the plunger 624 is urged forward into the barrel 622, the second locking tabs 649b snap into the groove 650, thus producing a distinct audible and tactile sensation indicating that needle retraction has been effected.

The force required to effect retraction is sufficiently high to minimize undesirable premature retraction, yet sufficiently low that the average person can effect retraction with one hand. Referring again to FIG. 11, the forward end of the device 620 is gripped during use, between the thumb and a forefinger of the dominant hand, with the rear of the device 620 aligned with the palm. In order to effect retraction, the doctor merely flexes the gripping thumb and finger firmly toward the palm while maintaining a natural grip on the device 620. Hence, the doctor does not need to be distracted from attending to the inserted catheter 700 in order to render the device 620 in a safe condition with the needle 625 retracted and to receive confirmation that the safety feature has been activated. Alternatively, needle retraction can be effected by any other technique for applying the predetermined actuating pressure to the rearwardly protruding flange 647 of the plunger 624.

When the plunger 624 has moved the latching projections or finger 637 to unlatch or release the needle head 630, the needle 625 is freed for retraction. As the head 630 of the needle 625 is freed, the spring 633 forces or shoots the needle head 630 and the attached needle 625 into the barrel 622. Of course, the device 620 is dimensioned to permit the entire length of the needle 625 to be received into the device 620 so that no portion of the needle 625 protrudes from the front alignment member 632 after retraction.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

That which is claimed is:

1. A medical device, having a forward end, comprising:
    a tubular barrel;
    a needle for puncturing the skin of a patient;
    a spring housing positioned in the forward end of the device having an aperture for aligning the needle therein such that the needle extends forwardly out of the device from within the spring housing;
    a spring positioned concentrically about the needle and compressed within the spring housing;
    a needle retainer forming the rear of the spring housing, the needle retainer comprising a plurality of axially extending resilient fingers for holding the needle within the spring housing against the expansive force exerted by the spring, the fingers having rearward facing angled surfaces for moving the finger; and
    an actuating member slidably positioned axially within the barrel, having a cavity formed therein for receiving the needle, and having a forward facing shoulder surface formed thereon to mate with the rearward angled surfaces of the fingers for forcibly moving the fingers out of engagement with the needle when the actuating member is urged in the forward direction within the tubular barrel, whereby the needle is released and propelled into the cavity.

2. The device of claim 1 wherein the actuating member comprises a tubular sleeve having a tapered forward end for providing the shoulder surface, and a frangible end member integrally formed with the tubular sleeve for closing the forward end of the cavity, the frangible end member being separable from the sleeve when the actuating member is urged forward to effect retraction of the needle.

3. The device of claim 2 wherein the actuating member has a longitudinal slot formed along a side of the sleeve and opening into the cavity.

4. The device of claim 1, wherein the fingers include radially inward extending hooks for providing an interior abutment surface at the rear of the spring housing, and further comprising a needle retaining member affixed to the rear of the needle, the needle retaining member providing a forward abutment surface for the rear end of the spring and a rear abutment surface for engagement with the interior abutment surface provided by the hooks.

5. The device of claim 1 wherein the device is a syringe hypodermic syringe.

6. The device of claim 1 wherein the device is a phlebotomy device.

7. The device of claim 1 comprising a catheter having a flexible cannula, wherein the needle supports the cannula.

8. A medical device, having a forward end, comprising:
    a tubular barrel;
    a needle for puncturing the skin of a patient;
    a spring housing positioned in the forward end of the device having an aperture for aligning the needle therein such that the needle extends forwardly out of the device from within the spring housing;
    a spring positioned concentrically about the needle and compressed within the spring housing;
    a needle retainer forming the rear of the spring housing, the needle retainer comprising a plurality of axially extending resilient fingers for holding the needle within the spring housing against the expansive force exerted by the spring, the fingers having rearward facing angled surfaces for moving the fingers; and
    an actuating member slidably positioned axially within the barrel, having a cavity formed therein for receiving the needle, and having a forward facing shoulder surface formed thereon to mate with the rearward angled surfaces of the fingers for forcibly moving the fingers out of engagement with the needle when the actuating member is urged in the forward direction within the tubular barrel, whereby the needle is released and propelled into the cavity;
    wherein the fingers include radially inward extending hooks for providing an interior abutment surface at the rear of the spring housing, and further comprising a needle retaining member affixed to the rear of the needle, the needle retaining member providing a forward abutment surface for the rear end of the spring and a rear abutment surface for engagement with the interior abutment surface provided by the hooks; and
    wherein the fingers and the hooks are mutually joined along respective sides thereof forming a fluid seal between the needle retaining member and the interior abutment surface for substantially preventing fluid from entering the spring housing from the interior of the barrel.

9. A medical device, having a forward end, comprising:
   a tubular barrel;
   a needle for puncturing the skin of a patient;
   a spring housing positioned in the forward end of the device having an aperture for aligning the needle therein such that the needle extends forwardly out of the device from within the spring housing;
   a spring positioned concentrically about the needle and compressed within the spring housing;
   a needle retainer forming the rear of the spring housing, the needle retainer comprising a plurality of axially extending resilient fingers for holding the needle within the spring housing against the expansive force exerted by the spring, the fingers having rearward facing angled surfaces for moving the fingers; and
   an actuating member slidably positioned axially within the barrel, having a cavity formed therein for receiving the needle, and having a forward facing shoulder surface formed thereon to mate with the rearward angled surfaces of the fingers for forcibly moving the fingers out of engagement with the needle when the actuating member is urged in the forward direction within the tubular barrel, whereby the needle is released and propelled into the cavity;
   wherein the fingers include radially inward extending hooks for providing an interior abutment surface at the rear of the spring housing, and further comprising a needle retaining member affixed to the rear of the needle, the needle retaining member providing a forward abutment surface for the rear end of the spring and a rear abutment surface for engagement with the interior abutment surface provided by the hooks; and
   wherein the needle retainer includes exterior grooves along the joints between the fingers to facilitate separation of the fingers when the needle is retracted.

10. A catheter insertion device comprising:
    a tubular barrel having an axial bore with a reduced diameter forward portion and an enlarged diameter rear portion;
    a catheter having a flexible cannula mounted to a catheter hub;
    a spring housing positioned in the forward portion of the barrel, having a nose portion a rear, and a front alignment aperture wherein the nose portion receives the interior of the catheter hub;
    a needle positioned axially in the spring housing and extending through the front alignment aperture for supporting and guiding the flexible cannula during insertion of the cannula into a patient;
    a spring compressed within the spring housing for exerting a rearward bias upon the needle;
    an actuating member positioned axially in the barrel, having a forward end, a rear actuating surface for allowing a user to urge the actuating member forward within the barrel, an engagement surface formed on the forward end of the actuating member for operatively engaging with the rear of the spring housing, and a central cavity formed therein for receiving the needle; and
    a needle retainer forming the rear of the spring housing, the needle retainer comprising a plurality of axially extending resilient fingers for holding the needle in position against the bias of the spring, the needle retainer having a rear engagement surface contoured to mate with the engagement surface of the actuating member such that the resilient figures are moved radially outward within the barrel for releasing the needle into the central cavity.

11. The catheter insertion device of claim 10 wherein the actuating member comprises a tubular sleeve with a frangible end member formed integrally on the forward end of the sleeve for sealing the central cavity and formed for separation from the sleeve when the actuating member is urged forward to effect retraction of the needle.

12. The catheter insertion device of claim 11 wherein the tubular sleeve has a longitudinal slot formed along a side thereof and opening into the central cavity.

13. The catheter insertion device of claim 10 wherein the actuating member comprises a tubular sleeve having a longitudinal slot formed along a side thereof and opening into the central cavity.

14. A medical device comprising:
    a housing;
    a needle having a sharpened tip, the needle being operable between a projecting position in which the sharpened tip projects forwardly from the housing, and a retracted position in which the sharpened tip is retracted within the housing;
    a spring circumscribing the needle, biasing the needle rearwardly toward the retracted position;
    a needle retainer for releasably retaining the needle in the projecting position, comprising:
       an axially elongated radially deformable element forming a latch for retaining the needle against the bias of the spring;
    a longitudinally elongated member axially displaceable within the housing; and
    a lock for impeding axial displacement of the elongated member after the needle is retracted;
    wherein upon application of an actuation force on the radially deformable element, the radially deformable element deforms radially, thereby permitting the needle to be propelled by the spring rearwardly toward the retracted position.

15. The medical device of claim 14 wherein the lock comprises a lip on one of the elongated member and the housing.

16. The medial device of claim 15 wherein the lock further comprises a tab projecting form the other of the elongated member and the housing.

17. The medical device of claim 14 wherein the housing has a rearward end and the lock is disposed adjacent the rearward end of the housing.

18. A medical device comprising:
    a housing having a rearward end;
    a needle having a sharpened tip, the needle being operable between a projecting position in which the sharpened tip projects forwardly from the housing, and a retracted position in which the sharpened tip is retracted within the housing;
    a spring circumscribing the needle, biasing the needle rearwardly toward the retracted position;
    a needle retainer for releasably retaining the needle in the projecting position, comprising:
       an axially elongated radially deformable element forming a latch for retaining the needle against the bias of the spring; and a lock disposed adjacent the rearward end of the housing for impeding axial displacement of the needle after the needle is retracted;

wherein upon application of an actuation force on the radially deformable element, the radially deformable finger deforms radially, thereby permitting the needle to be propelled by the spring rearwardly toward the retracted position.

* * * * *